(12) United States Patent
Magnussen et al.

(10) Patent No.: US 10,132,742 B2
(45) Date of Patent: Nov. 20, 2018

(54) PROBE UNIT WITH CLEANING MEANS

(71) Applicant: ProAnalysis AS, Bergen (NO)

(72) Inventors: Stian Magnussen, Bergen (NO); Hallvard Tangen, Bergen (NO); Anders Dalland, Bergen (NO); Bjørn Atle Øverland, Nesttun (NO); Sindre Rognved Hansen, Fotlandsvåg (NO); Øyvind Smith-Jahnsen, Blomsterdalen (NO)

(73) Assignee: ProAnalysis AS, Bergen (NO)

( * ) Notice: Subject to any disclaimer, the term of this patent is extended or adjusted under 35 U.S.C. 154(b) by 318 days.

(21) Appl. No.: 14/761,035

(22) PCT Filed: Jan. 17, 2014

(86) PCT No.: PCT/EP2014/050866
§ 371 (c)(1),
(2) Date: Jul. 15, 2015

(87) PCT Pub. No.: WO2014/111498
PCT Pub. Date: Jul. 24, 2014

(65) Prior Publication Data
US 2016/0025617 A1    Jan. 28, 2016

(30) Foreign Application Priority Data

Jan. 17, 2013   (NO) .................................. 20130103

(51) Int. Cl.
*G01N 21/15* (2006.01)
*G01N 21/85* (2006.01)
*B08B 3/12* (2006.01)

(52) U.S. Cl.
CPC ............... *G01N 21/15* (2013.01); *B08B 3/12* (2013.01); *G01N 21/8507* (2013.01);
(Continued)

(58) Field of Classification Search
CPC ............... G01N 21/15; G01N 21/8507; G01N 2021/151; G01N 2011/151;
(Continued)

(56) References Cited

U.S. PATENT DOCUMENTS

| 7,804,296 B2 | 9/2010 | Flaum et al. |
| 2005/0219541 A1 | 10/2005 | Johnson et al. |

(Continued)

FOREIGN PATENT DOCUMENTS

| DE | 19843553 A1 | 4/2000 |
| WO | WO-2009134145 A1 | 11/2009 |

OTHER PUBLICATIONS

Hoogen, Ricarda, "International Search Report," prepared for PCT/EP2014/050866, dated Apr. 24, 2014, four pages.

*Primary Examiner* — Robert R Raevis
(74) *Attorney, Agent, or Firm* — Winstead PC

(57) ABSTRACT

The present invention relates to a probe unit comprising a probe (2) having a probe window (3) having a contact surface for facing a high pressure fluid flow, the probe unit comprising a probe housing (1) containing the probe including the probe window, the probe being moveable relative to the probe housing between a first position wherein the window is exposed to the fluid flow and a second position wherein the probe is enclosed by said housing and a space (11) is defined between said housing and said probe, said housing having an outer part into said fluid flow, said probe unit comprising sealing means (4, 5, 7) adapted to seal said defined space from said fluid flow when the probe is in said second position. The probe unit also comprises pressure adjustment means for reducing the pressure within said space and cleaning means (6, 9) for cleaning said probe when within said space.

4 Claims, 4 Drawing Sheets

Figure 1A:
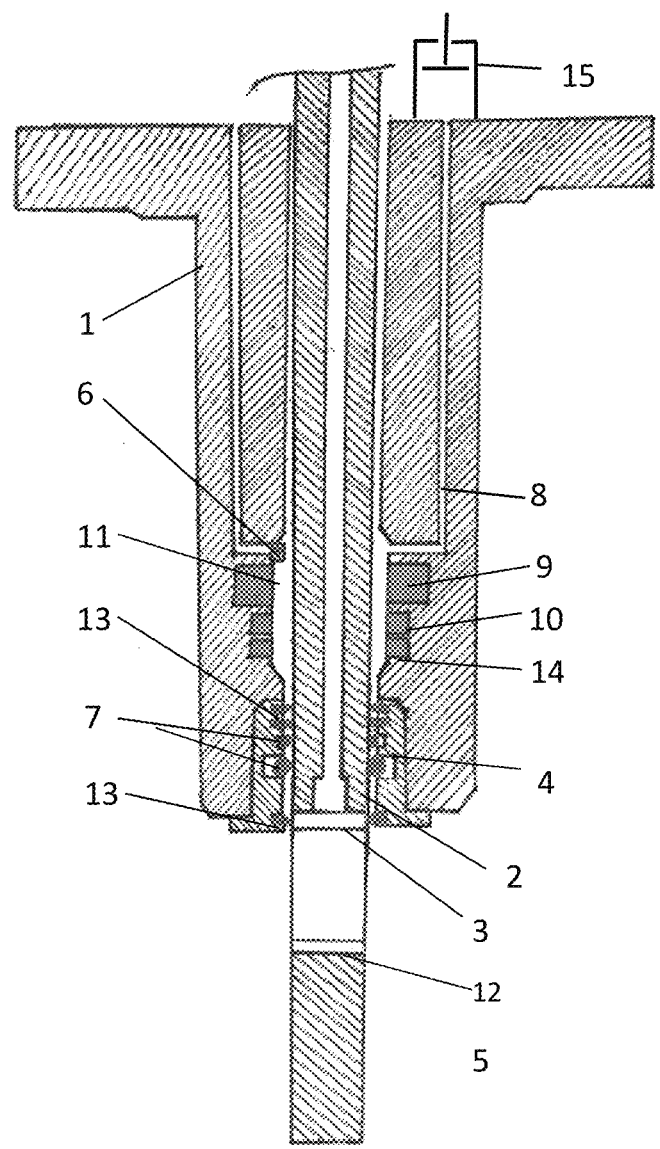

(52) U.S. Cl.
CPC . *G01N 2021/151* (2013.01); *G01N 2021/152* (2013.01); *G01N 2021/154* (2013.01); *G01N 2021/8514* (2013.01)

(58) Field of Classification Search
CPC ....... G01N 2021/152; G01N 2011/154; G01N 2021/155; G01N 2021/157; G01N 2021/158; G01N 2021/8514; B08B 3/12
USPC .......... 73/866.5, 24.01, 24.02, 31.05, 61.45, 73/61.48, 61.49, 61.68, 61.69, 293, 705, 73/865.8; 356/337–343, 436–442
See application file for complete search history.

(56) References Cited

U.S. PATENT DOCUMENTS

| | | | | |
|---|---|---|---|---|
| 2008/0212087 | A1* | 9/2008 | Mannhardt | G01N 21/15 356/244 |
| 2015/0285733 | A1* | 10/2015 | Henriksen | G01N 21/15 134/1 |

* cited by examiner

PROBE UNIT WITH CLEANING MEANS

This invention relates to a cleaning system for measuring instruments measuring chosen characteristics of a fluid medium contained in a pipe or container, especially for optical measuring probes for water, oil and/or gas flows. More specifically, the invention relates to a system for cleaning the window in front of or on the side of an optical measuring probe being positioned in a fluid medium by actively removing deposits.

In performing measurements in multiphase flows such as water, oil and/or gas flows, it is a well known problem that deposits form on the probe surface being in contact with the flow. This is especially relevant for optical probes, e.g. performing fluorescence measurements in the flow, as the probes comprise a transparent window toward the flow. If this window is covered by deposits it must be cleaned before measurements may continue. This cleaning may be performed by removing the probe from the flow, but this may be impractical and time consuming, in some cases requiring a local shut down of the system.

Several suggestions have been made to clean the window in situ. One example is discussed in U.S.2008/0212087, where a sensor for measuring particles at normal pressure may be retracted into a sleeve and the windows may be flushed with pressurized liquid. The sensor windows may be dried pressurized gas for drying it before reintroducing it into the measuring volume. In international patent application WO2009/134145 a sensor is discussed where the sensor window is cleaned during operation using an acoustic signal is used for cleaning the window in order to reduce the need for maintenance.

According to the recent development in the field measurements are being performed under high pressure, e.g in the range of 10-500 barg, but even higher pressures are being discussed. It is, however, known that most automated cleaning systems, eg flushing or acoustic cleaning are dependent on environmental conditions like pressure and temperature. Most methods eg flushing and acoustic cleaning become less efficient at higher pressures. Thus it is an object of the present invention to provide a means for cleaning a probe in a high pressure environment. This is obtained using a system and method according to the enclosed claims.

The present invention thus provides a means for isolating the probe window from the flow and then clean the window in an environment having a controlled and reduced pressure. The use for pressure chambers for monitoring properties of formation fluids is well known, as described in U.S. Pat. No. 7,804,296 where fluids are enclosed in a chamber being closed by valves, and the pressure is adjusted using a piston communicating with the chamber. In a high pressure subsea or downhole environment the use of valves will due to fouling and erosion mechanisms cause mechanical tear and wear, leading to costly and difficult maintenance, in contrary to the present invention.

Thus it is a further object to provide a low maintenance means for cleaning a probe surface under high pressures. These objects are obtained as stated in the accompanying claims.

Thus a means is provided for providing a low-pressure cleaning wherein the chamber provided with reduced pressure is defined between the probe and the probe housing with the use of additional valves or similar. These additional valves or similar will therefore be shielded from process fluid and can be exposed to but not limited to a different fluid flushing through the cleaning chamber. The term fluid in this specification includes both gas and liquid.

The invention will be discussed below with reference to the accompanying drawings, illustrating the invention by way of examples.

Figure 1B:
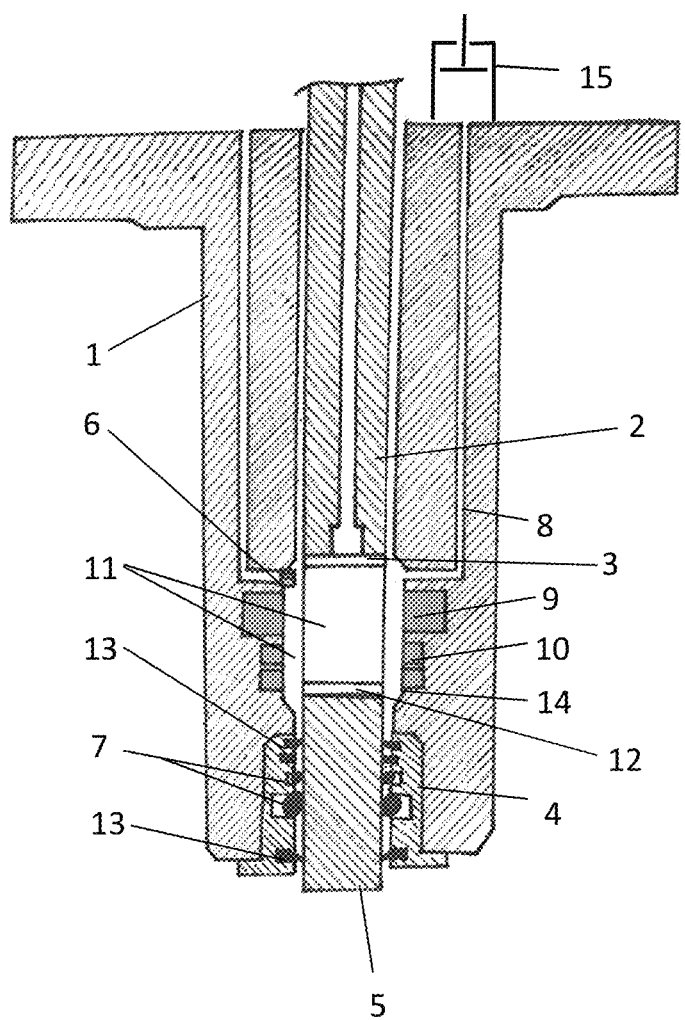

FIG. 1*a-b* illustrates at first probe unit according to the invention suitable for acoustic cleaning.

Figure 2A:
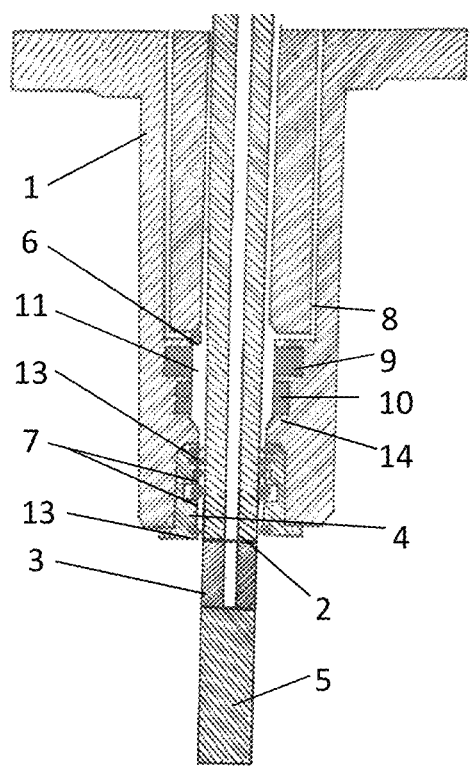
Figure 2B:
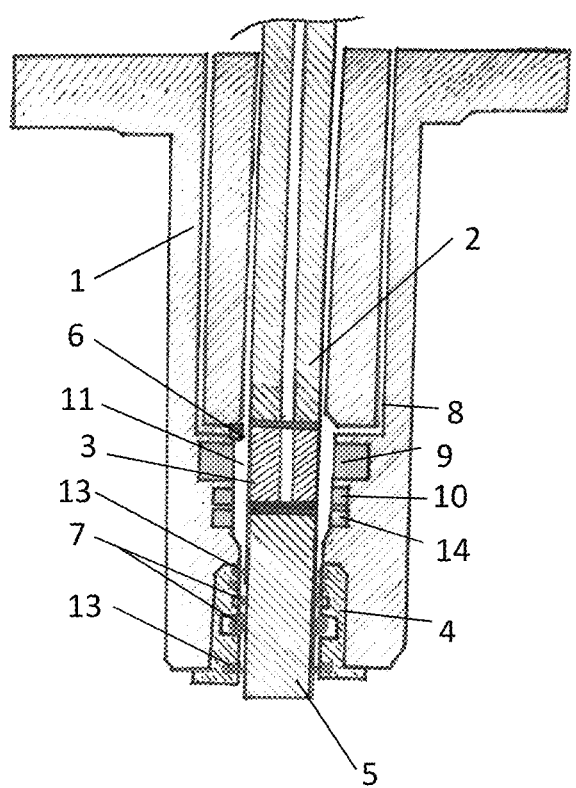

FIG. 2*a*-2*b* illustrates a second unit according to the invention suitable for a scraping section, pressurized cleaning fluid for flushing the probe window and indirect acoustic cleaning.

Thus the invention relates to a probe unit comprising a probe 2 having a probe window 3 with a contact surface facing a high pressure fluid flow, the probe unit comprising a probe housing 1 containing the probe 2 including the probe window 3. The probe housing is illustrated according to a preferred embodiment as a separate unit 1 to be mounted in a pipe or container wall through an opening gaining access to the fluid, but the housing may be more or less integrated in the pipe wall accepting the probe to through an opening or being welded into the pipe wall. One advantage in having a separate removable housing is for maintenance and/or for adapting to existing openings in the pipe or fluid container.

The probe 2 is moveable between minimum two positions relative to the probe housing between a first position (FIG. 1*a*, FIG. 2*a*) wherein the window is exposed to the fluid flow and a second position (FIG. 1*b*, FIG. 2*b*) where the window is enclosed by said housing defining a space or chamber 11 between said housing and said probe. The housing has an outer part into said fluid flow, the probe unit comprising sealing means 4 being adapted to seal the defined space from said fluid flow in when the probe 2 is in said second position. The probe unit comprises pressure adjustment means for reducing the pressure within said space and cleaning means for cleaning said probe when within said space. Pressure 10 and temperature 14 sensors may be positioned inside said housing 1 or in outer volume connected to the channels 8.

The sealing means 4 is constituted by a probe end 5 in the outer end of said probe, said probe end 5 having a shape corresponding with the shape of the outer part of said probe housing so as to seal said space when said probe is retracted into said second position. It also comprises O-rings 7 or equivalent in the probe housing interacting with the probe end 5, or alternatively the probe head 5 is provided with O-rings for interacting with the outer part of the opening in the probe housing.

In FIG. 1*a*-1*b* the probe is shown in an embodiment having a window surface in the axial direction, the probe end being connected to the probe using connection means such as rods extending from the window toward the probe end part 5, defining a space or chamber 11 between the probe end part 5 and the window 3. In optical measurements performed in the fluid flow the end part 5 may include a reflective part 12 facing the window 3 so that the light is emitted through the window and reflected back from this reflective part 12 as to provide a means of light intensity reference and reference to degree of contamination. In other embodiments the outer end is simply dimensioned and shaped so as to minimize the influence of the measuring conditions. In addition to optical measurements the principle according to the invention may also be relevant for other electromagnetic measurements incorporating a window interfacing the flow.

In the embodiment shown in FIG. 1*a*-1*b* the probe end also defines a volume between the window 3 and the probe end 5. When retracted into the housing the probe end 5 and sealing 4 provide an isolated chamber or space. The probe housing or probe may thus be provided with channels 8 for adjusting the volume and thus the pressure inside the space. The adjustment may be any suitable type, for example as described in U.S. Pat. No. 7,804,296 where a piston 15 is used to change the volume, but threaded screws or temperature changes may also be contemplated to provide a pressure adjustment.

Once inside the chamber a suitable cleaning method should be provided, for example an acoustic method as described in WO2009/134145 where the window is insonified by a transducer at the other end of the probe, the probe acting as a waveguide for the vibrations. These vibrations may also provide a cleaning effect on any windows or mirrors 12 on the probe inside the end part 5. It is also possible to provide acoustic transducers 9 in direct contact with the chamber between the window 3 and end part 5 for emitting the vibrations cleaning the window without applying vibrations to the probe.

The chamber may also be flushed with cleaning fluid in to help remove fouling in the chamber and increase cleaning effects.

In the embodiment according to FIG. 1*a*-1*b* a light source may be provided behind said mirror or window 12 as to provide a means to evaluate if cleaning is necessary.

Another embodiment of the invention is shown in FIG. 2*a*-2*b*, where the probe is rod 2 shaped having a radially oriented window 3 is positioned close to the probe end 5. The probe window in the FIG. 2*a*,2*b* is radially oriented in all directions from the probe axis, but may alternatively be positioned on one side of the probe, e.g. being oriented in the upstream or downstream direction only. As in FIGS. 1*a*-1*b* the probe and interacts with the outer end of the probe housing, e.g. with scraper rings 13 and O-rings 7, to seal the space when the probe 2 is in the retracted position inside the housing 1. In this case the scraper-rings provide some cleaning effect but as is shown the cleaning means is provided by pressurized flushing through nozzles 6 with cleaning fluid through a channel 8. The space or chamber 11 in this case may simply be the space between the probe, the probe housing and the sealing constituted by the probe head and outer housing, but a recess in the probe or probe housing may be contemplated.

In addition to or as an alternative to the abovementioned scraping and flushing cleaning within the chamber it is also possible to clean the window by indirect acoustic cleaning by transducers 9 and use suitable fluid supplied through channels 8. Both flushing and acoustic cleaning may be used at reduced pressure using said channels 8.

Thus to summarize the present invention relates to a probe unit comprising a probe having a probe window having a contact surface facing a high pressure fluid flow containing a process fluid. The probe unit comprising a probe housing containing the probe including the probe window, and the probe is moveable relative to the probe housing between a first position wherein the window is exposed to the fluid flow and a second position being enclosed by said housing defining a space between said housing and said probe. In the second position the probe unit provides a sealing means 4 adapted to seal a defined space inside the probe unit from the fluid flow in when the probe is in said second position. Thus by retracting the probe into the housing in the second position the sealed space is formed in which the pressure may be reduced, and a solution is provided without using valves and involving only one moveable part for obtaining a sealed space.

The probe unit comprises pressure adjustment means for reducing the pressure within said space that may include internal valves or pistons 15 for adjusting the pressure, and also cleaning means for cleaning said probe when within said space.

The sealing means 4 is preferably constituted by a probe end part 5 in the outer end of said probe, where the probe end has a shape corresponding with the shape of the outer part of said probe housing so as to seal said space when said probe is retracted into said second position. O-rings or similar may be provided in the coupling area between the probe end and the outer housing part.

The cleaning means may be one of several different solutions, but preferably includes acoustic transducer exiting said window 3 with vibrations having a chosen frequency. The acoustic transducer may be coupled directly to the probe window through the probe, as discussed in WO2009/134145 or by transmitting acoustic signals through the fluid inside the space toward the window. Alternatively, or in addition, the cleaning means may include a nozzle 6 flushing the window with a cleaning fluid.

As stated above it is essential for the present invention that the window 3 is retracted from a high pressure environment and the pressure is then reduced to a pressure where the cleaning is efficient. As discussed above this is important when using an acoustic cleaning method but also when using cleaning fluids. In both cases this also allows the fluid, e.g. the multiphase fluid from the flow, to be removed before cleaning, or the chamber or space 11 may be flushed or filled with a cleaning fluid after adapting the pressure within the chamber to the pressure in the environment, the fluid containers etc. This allows improved control over the cleaning process and it may also allow for calibration of the sensor with known fluids under controlled pressure. One option is to change the fluid in the chamber 11 before reducing the pressure. This has the advantage of avoiding chemical deposition and generation of scale in the chamber that may otherwise occur in the chamber when the pressure and temperature changes, thus improving the efficiency of the cleaning.

The preferred process according to the invention is thus as follows:

Retraction the probe window from the fluid flow.

Removing process fluid from the cleaning chamber 11, possibly exchanging it with water, cleaning fluid or by flushing.

Pressure reduction.

Cleaning by acoustic or flushing.

Pressure increase, preferably to flow pressure, to reduce wear on O-rings.

Positioning the probe back in measuring position.

This way precipitation of calcium carbonate and other scale mechanisms caused by phase changes may be prevented by exchanging the produced water with another liquid before reducing the pressure.

As illustrated in the drawings the space may be defined as the space between the window and the end part of the probe, or radially between the probe and the probe housing, or any combination of the two. The pressure adjustment means is preferably constituted by an adjustable piston connected to said space for adjusting the size of said space and thus the pressure.

The invention claimed is:

1. A probe unit comprising:
    a probe comprising a probe window the probe window comprising a contact surface facing a high pressure fluid flow containing a process fluid;
    a probe housing containing the probe including the probe window;
    the probe being moveable relative to the probe housing between a first position wherein the probe window is exposed to the fluid flow and a second position wherein the probe window is enclosed by the probe housing defining a space outside said probe window between the probe housing and the probe;

the probe housing having an outer part into the fluid flow;

sealing means adapted to seal the defined space from the fluid flow, the probe having an outer end and the sealing means comprising a seal between the outer end of the probe and the probe housing, the probe end having a shape corresponding with a shape of the outer part of the probe housing, so as to seal the space when the probe is retracted into the second position enclosing the defined space;

wherein the sealing means does not comprise a valve;

a pressure adjustment means for reducing the pressure within the space and a cleaning means for cleaning the probe when within the space when said pressure is reduced; and wherein the cleaning means comprises an acoustic transducer exciting the window or fluid in said space with vibrations having a chosen frequency.

2. The probe unit according to claim 1, wherein the cleaning means comprises a cleaning fluid flushed on the window.

3. The probe unit according to claim 1, wherein the pressure adjustment means comprises an adjustable piston connected to the space for adjusting the size of the space and thus the pressure.

4. The probe unit according to claim 1 wherein the process fluid is removed from the space after retraction into said probe housing.

* * * * *